United States Patent [19]

Keighley et al.

[11] Patent Number: 5,683,533
[45] Date of Patent: *Nov. 4, 1997

[54] METHOD FOR MANUFACTURING SIDE PANELS FOR DISPOSABLE ARTICLES

[75] Inventors: James A. Keighley, Wyoming; Donald L. Gerber, Cincinnati; Michael G. Nease; Mark D. Midkiff, both of Fairfield, all of Ohio

[73] Assignee: The Procter & Gamble Company, Cincinnati, Ohio

[*] Notice: The term of this patent shall not extend beyond the expiration date of Pat. No. 5,580,411.

[21] Appl. No.: 611,116

[22] Filed: Mar. 5, 1996

Related U.S. Application Data

[63] Continuation-in-part of Ser. No. 386,832, Feb. 10, 1995, Pat. No. 5,580,411.

[51] Int. Cl.⁶ .................... B31F 5/00; B32F 31/18; A61F 13/00
[52] U.S. Cl. .................... 156/204; 156/66; 156/256; 156/200; 156/270; 156/227; 604/385.1; 604/389
[58] Field of Search .................... 156/66, 199, 200, 156/204, 221, 227, 256, 269, 270, 260, 163, 264, 265, 259, 266, 263, 182, 512, 177, 160; 604/385.1, 385.2, 389, 390, 384

[56] References Cited

U.S. PATENT DOCUMENTS

| | | | |
|---|---|---|---|
| 3,875,837 | 4/1975 | Dussaud | 83/46 |
| 4,012,268 | 3/1977 | Johnsen | 156/200 |
| 4,670,960 | 6/1987 | Provost | 29/415 |
| 4,690,719 | 9/1987 | Lucas et al. | 156/201 |
| 4,704,115 | 11/1987 | Buell | 604/385.1 |
| 4,760,764 | 8/1988 | DeJonckheere et al. | 83/23 |
| 4,862,574 | 9/1989 | Seidy | 29/415 |
| 4,911,777 | 3/1990 | Truc et al. | 156/256 |
| 4,938,753 | 7/1990 | Van Gompel et al. | 604/385.2 |
| 4,940,464 | 7/1990 | Van Gompel et al. | 604/396 |
| 4,980,007 | 12/1990 | Ferguson | 156/267 |
| 5,034,007 | 7/1991 | Igaue et al. | 604/365 |
| 5,110,386 | 5/1992 | Ochi et al. | 156/204 |
| 5,156,793 | 10/1992 | Buell et al. | 264/288.8 |
| 5,167,897 | 12/1992 | Weber et al. | 264/288.8 |
| 5,354,400 | 10/1994 | Lavash et al. | 156/227 |
| 5,354,408 | 10/1994 | Otomine et al. | 156/517 |
| 5,399,219 | 3/1995 | Roessler et al. | 156/259 |
| 5,580,411 | 12/1996 | Nease et al. | 156/260 |

FOREIGN PATENT DOCUMENTS

| | | | |
|---|---|---|---|
| 0 233 704 | 8/1987 | European Pat. Off. | A61F 5/44 |
| 0 539 032 A1 | 4/1993 | European Pat. Off. | A61F 13/15 |

*Primary Examiner*—David A. Simmons
*Assistant Examiner*—Linda L. Gray
*Attorney, Agent, or Firm*—David M. Weirich; Steven W. Miller; Jacobus C. Rasser

[57] ABSTRACT

A method for manufacturing side panels for use with disposable articles including the following steps: providing a web of material in a machine direction, the web having activation zones and designated final cut regions; activating the activation zones; making a series of intermediate cuts in the web, each of the intermediate cuts extending across at least a portion of one of the activation zones; making a folded web by folding the web along an axis that is generally parallel to said machine direction; and cutting the folded web in the designated final cut regions to provide individual extensible side panels.

38 Claims, 8 Drawing Sheets

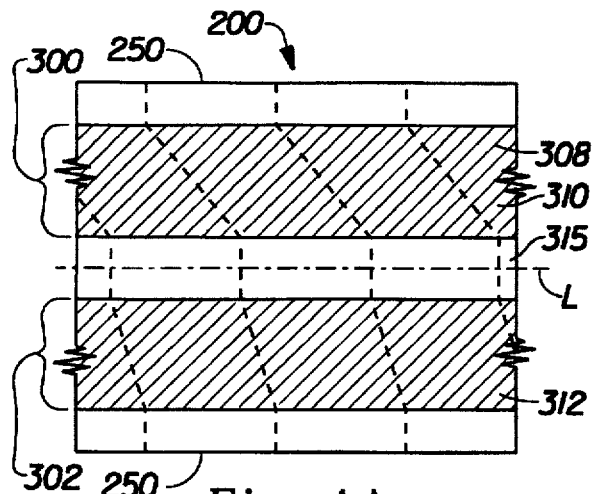
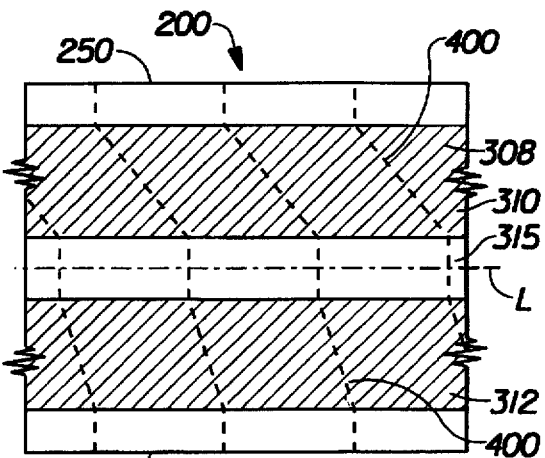
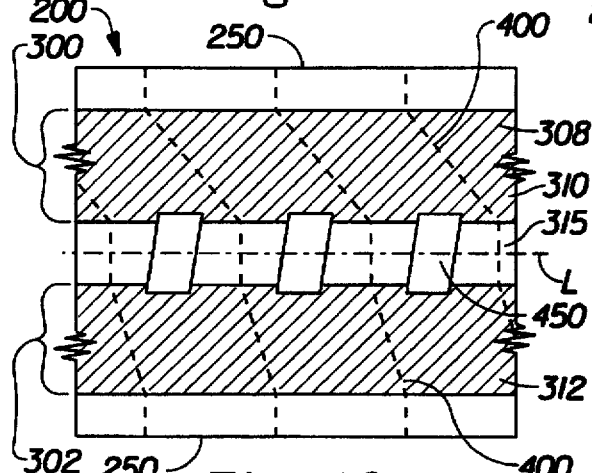
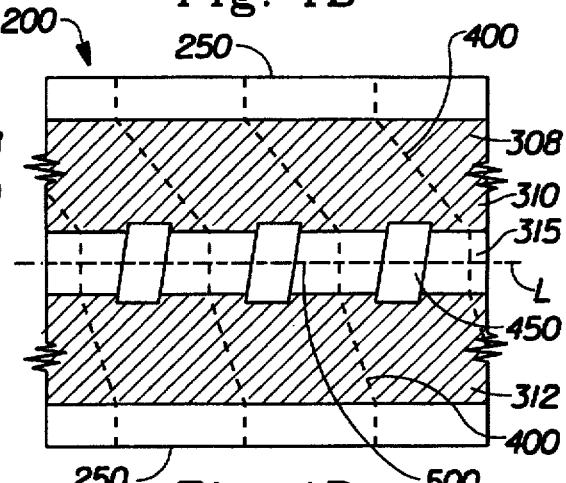
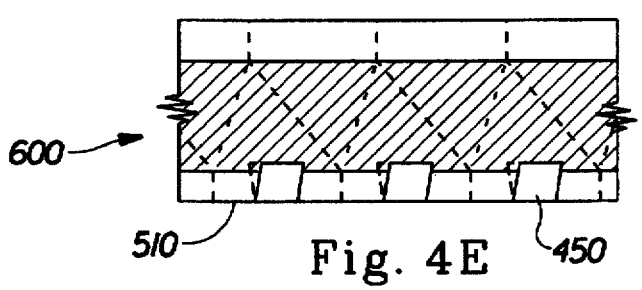
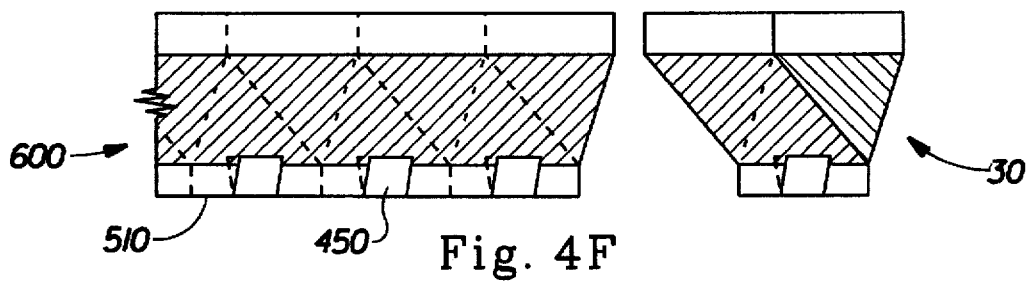

METHOD FOR MANUFACTURING SIDE PANELS FOR DISPOSABLE ARTICLES

This application is a continuation-in-part of U.S. patent application Ser. No. 08/386,832, filed Feb. 10, 1995, which issued as U.S. Pat. No. 5,580,411 on Dec. 3, 1996 in the names of Nease et al.

FIELD OF THE INVENTION

This invention relates to a method for manufacturing side panels for disposable and/or absorbent articles, and more particularly to a method of manufacturing elastically extensible side panels for disposable absorbent articles that produces little or no scrap at relatively high speeds.

BACKGROUND OF THE INVENTION

Absorbent articles such as diapers, training pants, incontinence garments, feminine hygiene garments, under pants, panties and the like have become very popular in the market place today. Many of these articles are disposable (i.e. generally intended to be used only once and then thrown away, rather than laundered). Others are intended to be reused one or more times after the initial use. In any case, advances in the technology have provided many improvements over the absorbent articles of the past. Today, many of these articles include improved containment characteristics and better, more comfortable fit. One feature that has been found to help provide such improvements is the side panel, and more particularly extensible side panels.

An overriding consideration in the construction of absorbent articles, especially disposable articles, is the cost of manufacturing the article, including the materials cost. The present invention provides a method for manufacturing side panels for absorbent articles with little or no wasted material. The process also provides a simplified process for manufacturing side panels that can be run at relatively high speeds. The high production speeds provided by the method of the present invention allow side panels to be manufactured "on-line", concurrently with the article to which they will be attached, or can be used to produce side panels at a different time or location which can then be brought to the disposable article manufacturing line as needed. Thus, the process of the present invention can provide lower cost side panels at high speeds with little or no waste.

In one preferred embodiment of the present invention, multi-directional extensible side panels can be produced. Other methods for producing such multi-directional extensible side panels often included complicated sequences of cutting and aligning the side panel materials. The method of the present invention, however, provides a simplified process which allows for the economical manufacture of multi-directional extensible side panels at very high speeds with little or no waste. Therefore, the side panels can be, if desired, manufactured on-line with the absorbent articles to which they are to be attached. Accordingly, the method of the present invention can reduce the overall cost of the absorbent articles.

Therefore, it is an object of the present invention to provide a method for manufacturing side panels for absorbent articles with little or no waste.

It is a further object of the present invention to provide a method for manufacturing side panels for absorbent articles at relatively high speeds.

It is a further object of the present invention to provide a method for manufacturing relatively low cost side panels for absorbent articles.

It is yet a further object of the present invention to provide a method for manufacturing "zero scrap", low cost, elastically extensible side panels for use with absorbent articles.

It is still a further object of the present invention to provide a method for manufacturing little or no scrap, multi-directional side panel for use with absorbent articles.

SUMMARY OF THE INVENTION

The present invention provides a method for manufacturing side panels for use with disposable and/or absorbent articles that produces little scrap and can be run at high speeds. In one preferred embodiment, the present invention provides a zero scrap method for manufacturing multi-directional extensible side panels including the following steps: (a) providing a web of material in a machine direction, the web having predetermined activation zones and designated final cut regions; (b) activating the predetermined activation zones; (c) making a series of intermediate cuts in the web, each of the intermediate cuts extending across at least a portion of one of the activation zones; (d) folding the web along an axis that is generally parallel to said machine direction; and (e) cutting the folded web in the designated final cut regions to provide individual extensible side panels.

BRIEF DESCRIPTION OF THE DRAWINGS

While the specification concludes with claims particularly pointing out and distinctly claiming the subject matter which is regarded as the present invention, it is believed that the invention will be better understood from the following description taken in conjunction with the accompanying drawings, in which:

FIGS. 4A–F are plan views of the side panels produced by one embodiment of the method of the present invention shown as they would look at certain different stages in the process;

DETAILED DESCRIPTION OF THE INVENTION

The method of the present invention is particularly suited for manufacturing side panels for use with disposable absorbent articles, and thus, will be described hereafter in terms of such disposable absorbent articles. However, it should be noted that the method can be used to produce side panels for articles disposable and not necessarily absorbent, as well as articles that are absorbent but not necessarily disposable, as defined hereafter. The term "absorbent article" refers to devices which absorb and contain body exudates, and more specifically, refers to devices which are placed against the skin of a wearer to absorb and contain the various exudates discharged from the body. The term "disposable" is used herein to describe absorbent articles which are not intended to be laundered or otherwise restored or reused as an absorbent article after a single use (i.e. they are intended to be discarded, and preferably, recycled, composted or otherwise disposed of in an environmentally compatible manner). A "unitary" absorbent article refers to an absorbent article which is formed from separate parts united together to form a coordinated entity so that they do not require separate manipulative parts like a separate holder and liner. As used herein, the term "zero scrap" refers to a method of manufacturing side panels that produces little or no wasted material.

Figure 1:
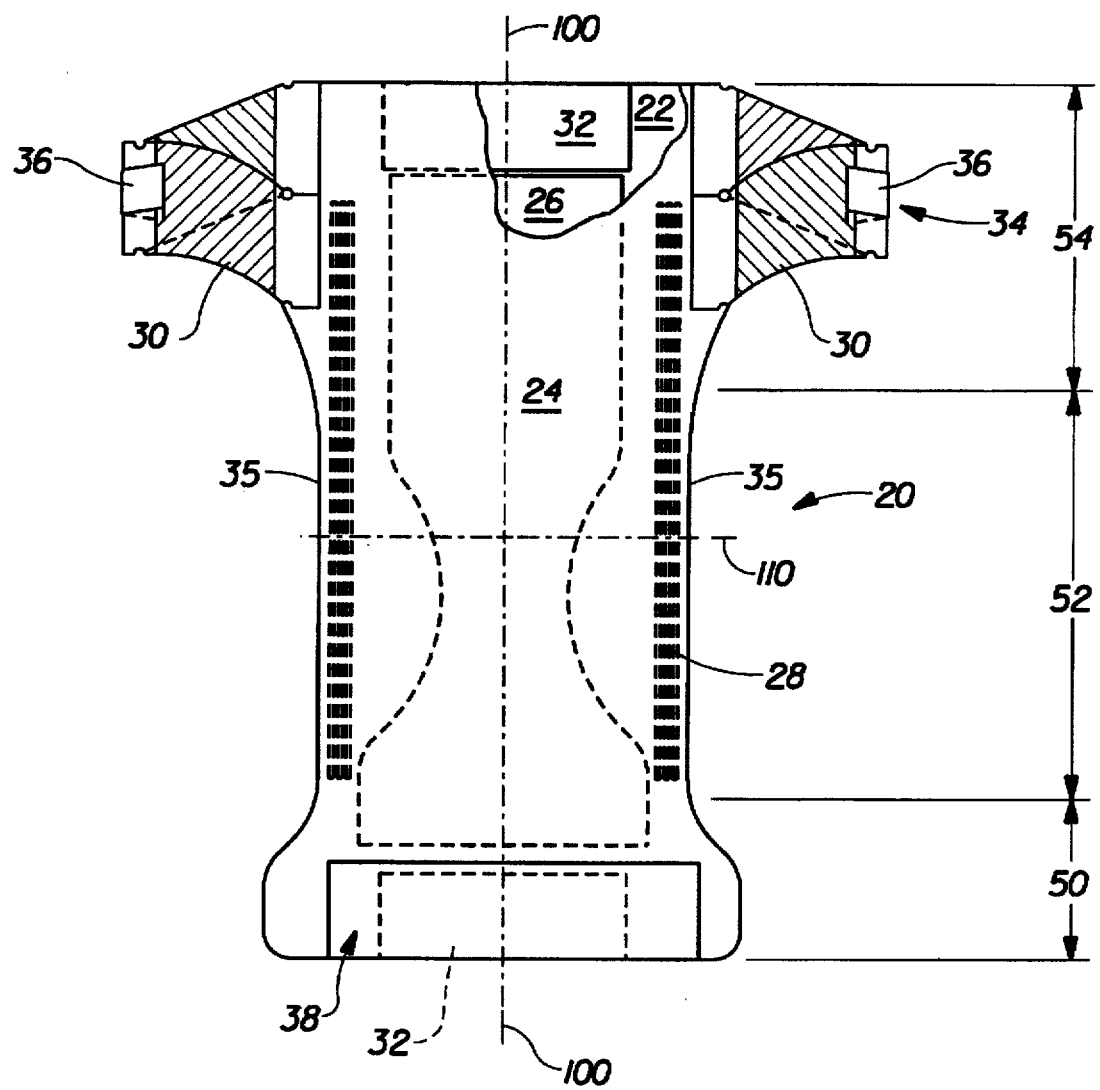
FIG. 1 is a plan view of a disposable article comprising side panels manufactured in accordance with the method of the present invention.

A preferred embodiment of a unitary absorbent article comprising tape tabs and/or mechanical fasteners having side panels 30 manufactured by the method of the present invention is the diaper 20 shown in FIG. 1. As used herein, the term "diaper" refers to an absorbent article generally worn by infants and incontinent persons that is generally worn about the lower torso of the wearer. It should be understood, however, that the present invention is also applicable to other disposable articles such as incontinence briefs, diaper holders, feminine hygiene garments, training pants, panties, under pants and the like.

FIG. 1 shows an example of a preferred diaper 20, having a front waist region 50, a rear waist region 54 opposed the front waist region 50 and a crotch region 52 located between the front waist region 50 and the rear waist region 54. Such diapers generally comprise a liquid permeable topsheet 22, a liquid impermeable backsheet 24, and an absorbent core 26 between the topsheet 22 and the backsheet 24. The diaper 20 preferably further comprises elasticized leg cuffs 28, side panels 30, an elastic waist feature 32 and a fastening system 34 which may comprise fasteners 36 and landing zone 38. An example of an absorbent article to which the side panels 30 of the present invention may be joined is more fully and completely described in U.S. Pat. No. 5,151,092, entitled "Absorbent Article With Dynamic Elastic Waist Feature Having a Predisposed Resilient Flexural Hinge", issued to Buell et al., on Sep. 29, 1992; and the commonly assigned, copending U.S. patent application Ser. No. 08/155,048 entitled "Absorbent Article with Multi-directional Extensible Side Panels", filed on Nov. 19, 1993 in the names of Robles, et al., which is hereby incorporated by reference herein.

Method for Manufacturing Side Panels

Figure 2:
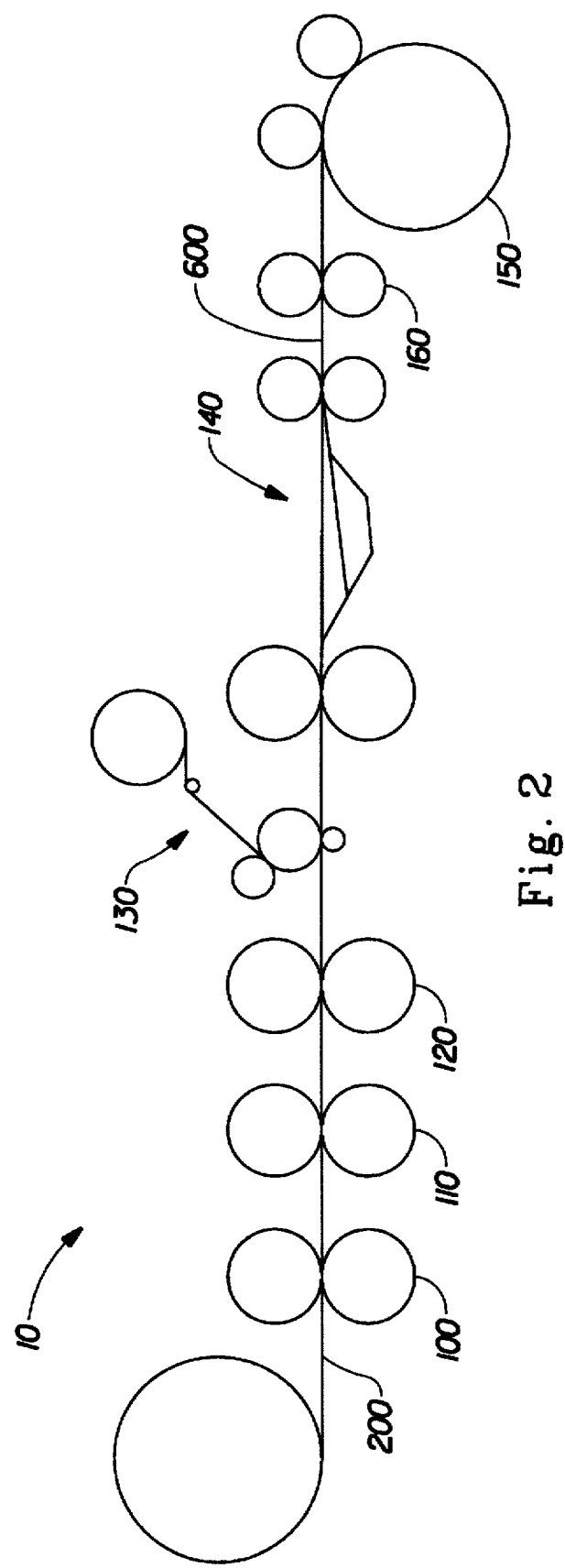
FIG. 2 is a schematic side view of one embodiment of the side panel making process.
Figure 5:
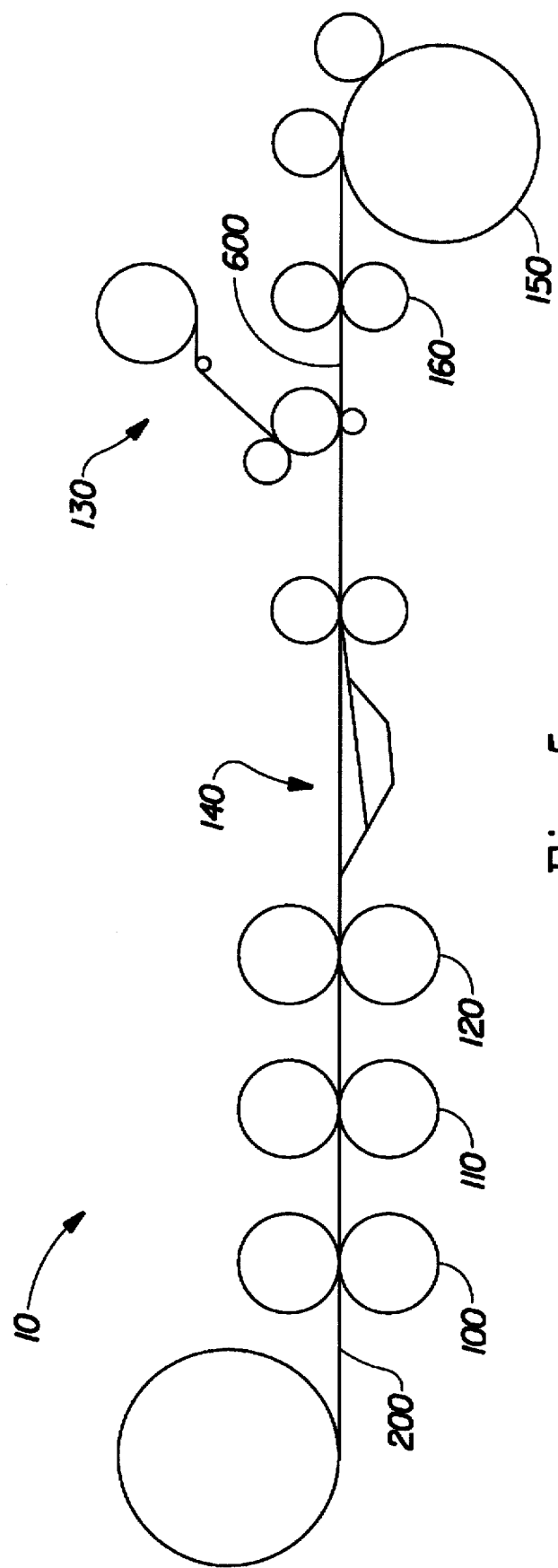
FIG. 5 is a schematic side view of one embodiment of the side panel making process.

The side panels 30 may be produced on the apparatus 10 shown in FIGS. 2 and 5. In one preferred embodiment, the apparatus 10 is integrated into a disposable absorbent article manufacturing line such that the side panels 30 may be manufactured "on-line". (As used herein, the term "integrated" refers to interconnected process modules that operate concurrently to produce finished products from source materials. The term "on-line" is used to refer to the process of manufacturing the side panels 30 on an apparatus that is integrated with the manufacturing line that produces the disposable absorbent articles to which the side panels 30 will be joined.) However, embodiments are contemplated wherein the side panels 30 are produced off-line and subsequently brought to the place at which they will be joined with the absorbent articles.

Examining one embodiment of the process in greater detail, as shown in FIG. 2, the web of material from which the side panels 30 are made is first provided to the apparatus 10. The web 200 preferably has a longitudinal centerline L and two longitudinal edges, all of which extend in a direction generally parallel to the machine direction. The web 200 also has a first region 300, a second region 302 and preferably a central zone 315. The central zone 315, if any, is preferably located between the first region 300 and the second region 302.

The web 200 may be made "on-line" in a process preceding the process for manufacturing the side panels 30, or the material may be produced off-line and brought to the side panel manufacturing apparatus 10. Despite the origin or process used to make the material from which the side panels 30 are produced, the material preferably comprises a laminate of more than one stock material. (However, it should be noted that the side panels 30 may be produced from a single stock material.) In a preferred embodiment, the material comprises a laminate of polyethylene film, a filler material and a nonwoven material. The materials are preferably combined together by any means known in the art for combining such materials into laminate structures. Some examples of suitable joining means include, but are not limited to, adhesives, heat, ultrasound, pressure, coextrusion and the like.

One example of a suitable polyethylene film is available from the Clopay Corporation of Cincinnati, Ohio. under the trade designation Clopay 1401. Other materials which may be used in place of or in combination with the preferred polyethylene film include, but are not limited to polyolefins such as polyethylenes, including linear low density polyethylene, low density polyethylene, ultra low density polyethylene, high density polyethylene, polypropylene, polyester, polyurethane, compostable or biodegradable polymers, heat shrink polymers, thermoplastic polymers, metallocene catalyst based polymers (e.g., INSITE available from Dow Chemical Company, EXXACT available from Exxon and CPC2 polyethylene available from Tredegar, Inc.).

Suitable filler materials include, but are not limited to the apertured formed films available from Tredegar Film Products, Inc. of Terre Haute, Ind., two-dimensional apertured films, macroscopically expanded, three-dimensional apertured formed films, polymer films, nonwovens, foams, thermally bonded air-laid fibrous structures and composites or laminates of any of the above. Other filler materials are described in U.S. Pat. No. 4,342,314 issued to Radel, et al.; U.S. Pat. No. 4,463,045 issued to Ahr et al.; U.S. Pat. No. 3,929,135 issued to Thompson; U.S. Pat. No. 4,324,246 issued to Mullane, et al.; and U.S. Pat. No. 5,006,394 issued to Baird. Each of these patents are incorporated by reference herein.

An acceptable nonwoven can be obtained from Fiberweb North America, Inc. of Greenville, S.C. under the trade designation P-14. However, other suitable nonwovens include, but are not limited to those comprising natural fibers such as cotton or wool; synthetic fibers of nylon, polyamides, polyesters, or polyolefins; yarns; polyethylene; polypropylene or any combination of these or other materials known in the art. The nonwoven webs may be manufactured in any of the following ways: spunlace, spunbond, meltblown, carded, air-through, calender bonded or any other method that is known in the art.

Once the side panel laminate 200 is formed the laminate 200 is preferably fed into the side panel manufacturing apparatus 10. The laminate 200 may be fed into the apparatus 10 by any system known in the art. In a preferred embodiment the system comprises a tensioning device and a metering device. The laminate 200 is preferably tensioned by means of a standard tensioning device, commonly known in the art as a dancer. The metering device, such as a powered roll or S wrap, feeds the laminate 200 into side panel manufacturing apparatus 10 at the desired speed. Suitable systems for feeding the laminate 200 into the apparatus 10 are available from the Curt G. Joa Corporation of Sheboygan Falls, Wis. and from the Machintek Corporation of Fairfield, Ohio. After the laminate 200 is fed into the process, it is preferably passes through a tracking device 100, as is commonly known in the art, to align the laminate for subsequent processing. Examples of suitable tracking devices are manufactured by the Fife Corporation of Oklahoma City, Okla. under the trade designations FIFE A9 or FIFE SYMAT 25.

After the laminate 200 has been aligned by the tracking device 100, it may proceed to an activating device 110 which mechanically activates the laminate 200. However, it should be understood that the activation step may be performed at any point in the process, preferably prior to the time at which the laminate 200 is folded as described below. Also, embodiments are contemplated wherein the laminate 200 comprises material(s) which are elastically extensible without the need for an activation step. In such cases, the materials may be further activated as described below, or may be processed into the final product without an activation step. (As used herein, the term "activated" means to impart elasticity in the material such that the material may elastically extend in one or more directions. Examples of preferred mechanical activation methods are described in the patents listed below. "Elastically extensible" materials extend in at least one direction when a force is applied and return to approximately their original dimensions after the force is removed.) The laminate 200 may be activated by any means as are known in the art, including, but not limited to ring rolling, embossing, thermoforming, high pressure hydraulic forming or casting. These means for providing elasticity to the laminate 200, and other activation means not mentioned, obviate the need for additional elastomeric materials. Such methods are generally preferred over methods for imparting elasticity into the laminate which include the addition of an elastomeric material or materials. However, embodiments of the present invention are contemplated wherein additional elastomeric materials such as elastic, natural or synthetic rubber, rubber foams, elastomeric scrims, woven or nonwoven elastomeric webs, elastomeric composites, zero-strain stretch laminates, prestrained stretch laminates or the like are used, alone or in combination with any of the other methods described herein, to provide elasticity to the laminate 200. Some examples of preferred methods for imparting elasticity to the laminate 200 are described in detail in U.S. Pat. No. 5,156,793 entitled "Method for Incrementally Stretching Zero Strain Stretch Laminate Web in a Nonuniform Manner to Impart a Varying Degree of Elasticity Thereto", issued to Buell et al., on Oct. 20, 1992; U.S. Pat. No. 5,167,897 entitled "Method for Incrementally Stretching a Zero Strain Stretch Laminate Web to Impart Elasticity Thereto", issued to Weber et al., on Dec. 1, 1992; and co-pending U.S. patent application Ser. No. 08/203,087 entitled "Web Materials Exhibiting Elastic-Like Behavior", filed in the names of Chappell et al., on Feb. 28, 1994 (International Application WO 9503765, published Feb. 9, 1995). Each of the above-identified U.S. Patents and other references are hereby incorporated by reference herein.

Figure 6:
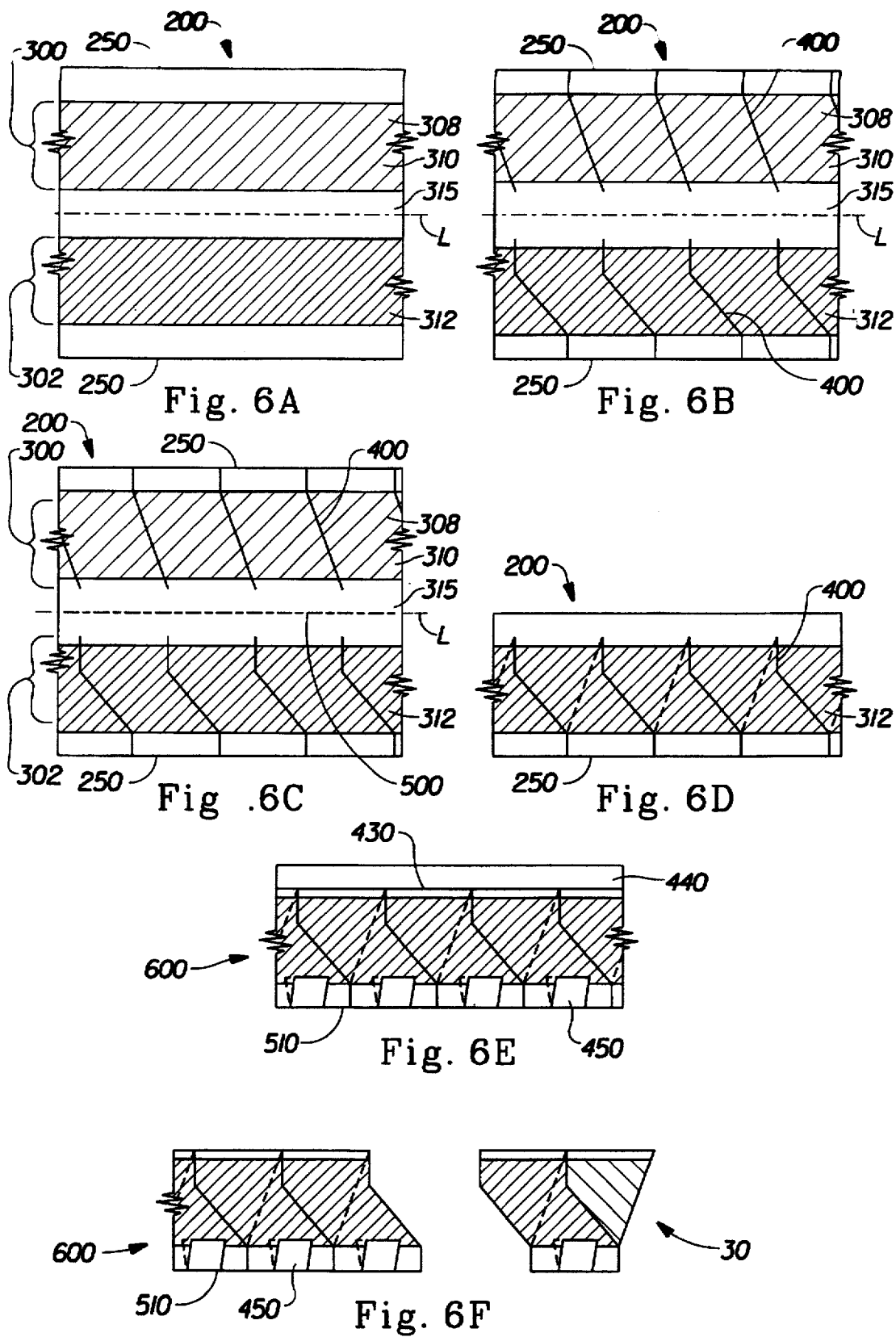
FIGS. 6A–6F are plan views of the side panels produced by one embodiment of the method of the present invention shown as they would look at certain different stages in the process.

Preferred patterns of activation 308 are generally shown in FIGS. 3A–F, 4A–F and 6A–F. The pattern 308 gives the side panels 30 multi-directional stretch characteristics when the side panels 30 are constructed according to the method steps that follow. Further, the pattern 308 can be easily made as the laminate 200 moves through the activating device 110 in the machine direction and may be continuous or phased. (As used herein, the term "machine direction" refers to the general direction in which the materials being processed move. The term "cross machine direction" is the direction generally perpendicular to the machine direction. As used herein, the terms "phased" or "in phase" means that the activation pattern 308 is controlled in such that it is continuously repeated so as to coincides with predetermined portions of the laminate 200.) Other patterns of activation 308 are contemplated, including, but not limited to nonuniform patterns, or wherein the pattern of activation 308 may comprise several different regions of activation that provide the laminate 200 or portions of the laminate 200 with different mounts or directions of elasticity. An example of a side panel comprising varying patterns of activation is illustrated in FIG. 6F.

In a preferred embodiments, as shown in FIGS. 3A–D, 4A–D and 6A–D, the laminate 200 is activated in at least two predetermined activation zones, a first activation zone 310 and a second activation zone 312. The first activation zone 310 is preferably located in at least the first region 300 and the second activation zone 312 is preferably located in at least the second region 302 Preferably the first and second activation zones 310 and 312 are separated by a central zone 315, the size of which may vary dependent on the desired characteristics of the side panels 30. (It should be noted that embodiments are contemplated wherein the central zone 315 is activated. In such embodiments, the activation in the central zone 315 may be the same as either or both of the first and second activated zones 310 and 312, or may be different from the activated zones 310 and 312.) Preferably, the first and second activated zones 310 and 312 run generally parallel to the machine direction. (As used herein, the term "generally parallel" refers to lines of direction that are parallel to or at an angle of less than 45 degrees from the direction from which the line of direction is being measured. The term "generally perpendicular" refers to lines of direction that are perpendicular to or at an angle of more than 45 degrees from the direction from which the line of direction is being measured.) Each of the zones 310 and 312 may be activated by the same methods or by different methods and at the same or different times. Further, the size of the zones 310 and 312 and their orientation about the central zone 315, if any, may be the same or different. (Although it should be recostnized that activation zones are not necessary in some embodiments, to simplify the description of the invention, most of the remainder of the specification will be described in terms of an embodiment having at least two activated zones.)

The laminate 200 is preferably subjected to a series of intermediate cuts 400. The intermediate cuts 400 serve to define the waist and leg edges of the individual side panels resulting from the method described herein. The intermediate cuts 400 are preferably made by a slitting device 120. The slitting device 120 may be any device that can slit, score or perforate the laminate 200. (Alternative embodiments are envisioned, however, wherein the laminate 200 is chemically etched or mechanically weakened instead of being slit, cut or perforated.) A preferred slitting device is a standard die cutting assembly commonly known in the art. In another preferred embodiment, the slitting device 120 comprises anvil rolls having vacuum holes that hold the laminate 200 in place while it is slit. Further, in some embodiments, it is preferred that the slitting device 120 be close coupled or driven from the same drive as the activation unit 110 or a hole punching unit (not shown) so that the intermediate cuts 400 can be maintained in phase with the activation pattern 308.

A hole punch unit (not shown) may be incorporated into the apparatus 10 to provide registration holes 410 in the laminate 200. The registration holes 410 may be useful to maintain the laminate 200 in phase with any other step of the process, to move the laminate 200 through the apparatus or may act as termination regions for the intermediate cuts 400 or final cuts 425. The holes 410 may be cut or punched into the laminate 200 at any desirable point in the process and the hole punch unit may be any unit capable of punching or cutting holes in the laminate 200. Such units are well known in the art and may be incorporated into or be separate from the slitting device 120 or any other device incorporated into the apparatus 10. In one preferred embodiment, registration holes 410 are provided in the laminate 200 after it has been folded, as described below.

Figure 3A:
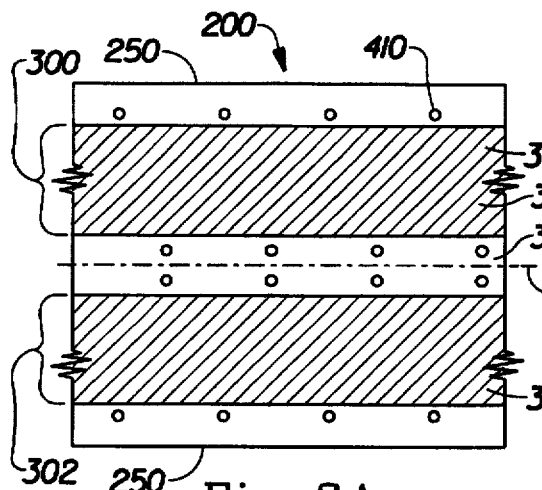
FIGS. 3A–F are plan views of the side panels produced by one embodiment of the method of the present invention shown as they would look at certain different stages in the process.
Figure 3B:
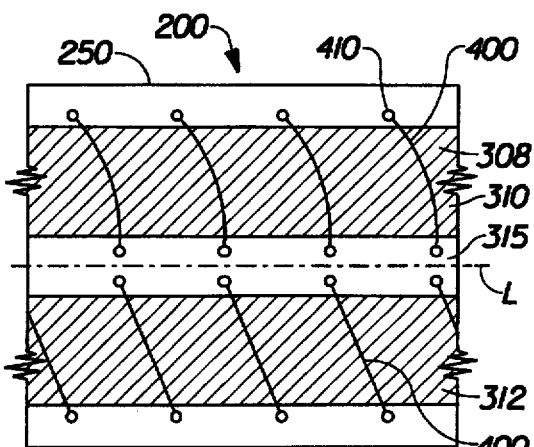
Figure 3C:
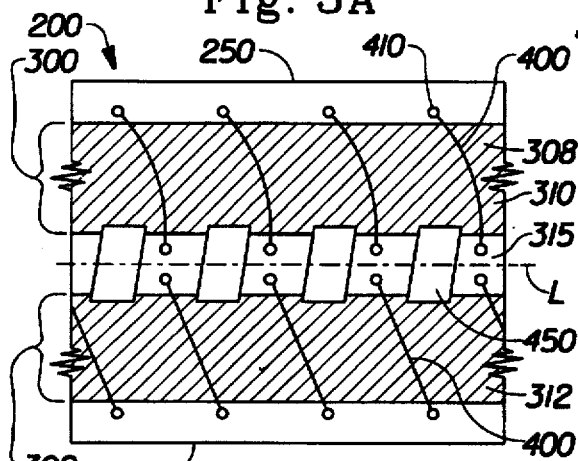
Figure 3D:
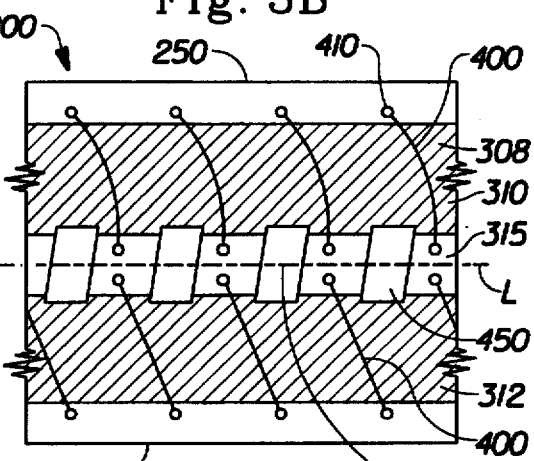

FIGS. 3B–D, 4B–D and 6B–D show three examples of the intermediate cuts 400 that may be used in the method of the present invention. The intermediate cuts 400 may be any length, shape, width or orientation that will provide suitable side panels 30. For example, the intermediate cuts may be continuous, intermittent, straight, curvilinear, or irregular. Further, as shown in FIGS. 3B–D, the intermediate cuts that extend across the different activated zones 310 and 312 may be different. Embodiments are also contemplated wherein the intermediate cuts 400 extending across a single activated zone may be different from each other. In general, it is preferred that the intermediate cuts 400 are generally perpendicular to the machine direction. It is also preferred that the intermediate cuts 400 form a generally repetitive pattern extending at least partially across the first activated zone 310 and separately at least partially across the second activated zone 312. It may also be preferred in some embodiments that the intermediate cuts 400 do not extend all the way across the central region 315, if any, or cross from one activated zone into another. For handling and other purposes it may also be preferred that the intermediate cuts 400 do not reach the longitudinal side edges 250 of the laminate 200. In one preferred embodiment, as shown in FIGS. A–D, the intermediate cuts 400 extend entirely across each activated zone 310 and 312 from one registration hole 410 to a corresponding registration hole 410 located on the opposite side of the activated zone.

FIGS. 4A–F depict an alternative preferred embodiment of the present invention wherein the laminate 200 has intermediate cuts 400 comprising perforations. The intermediate cuts 400 in this embodiment are shown to extend entirely across the laminate 200 in a direction generally perpendicular to the longitudinal centerline L. In embodiments having two zones of activation, the intermediate cuts 400 would preferably extend across both zones of activation 310 and 312 and through the central region 315, if any, from one longitudinal edge 250 of the laminate 200 to the other longitudinal edge 250.

Fastening elements 450 are preferably joined to the laminate 200 by the fastener providing device 130, as shown in FIGS. 2 and 5. The fastener providing device may be any suitable unit that can provide and join fastening elements 450 to the laminate 200. The fastener providing device 130 may produce all or portions of each fastening element 450 or may serve to provide and join the fastening elements 450 to the laminate 200. Thus, the fastener providing device 130 may be any known tape tab, mechanical fastener or other fastener making or providing device. Examples of suitable methods for making tape tabs on-line are described in U.S. Pat. Nos. 5,482,588 entitled "Method For Manufacturing One-Piece Tape Tab Fasteners For Use With Disposable Absorbent Articles"; and 5,487,809 entitled "method For Manufacturing Tape Tab Stock That May Be Used To Produce Tape Tab Fasteners For Absorbent Articles", issued to Goulait et al. on Jan. 9, 1996 and Jan. 30, 1996, respectively. These patents are hereby incorporated by reference herein.

In preferred embodiments, the fastening elements 450 are located in at least a portion of the central region 315. This configuration allows for the fastening elements 450 to be disposed adjacent the distal edges 45 of the side panels 30 in their final form. The fastening elements 450 may be joined to the laminate 200 at any point during the process of making the side panels 30. In some instances, it may be advantageous to leave the fastening elements 450 off of the side panels 30 until some time after the side panels 30 have been formed. In such cases, the fastening elements 450 can be joined to the side panels 30 after the side panels 30 have been formed but prior to the side panels 30 being joined to the absorbent article 20 or after the side panels 30 are joined to the article. Further, any known method can be used to join the fastening elements 450 to the laminate 200 or the completed side panels 30. Some examples of suitable methods for joining the fastening elements 450 include, but are not limited to, adhesives, cohesives, heat bonding, pressure bonding, ultrasonic bonding, or any combination of any known methods of joining such materials.

The laminate 200 is preferably mechanically or chemically manipulated in such a way that it may be easily folded along the resulting crease 500. (However, embodiments are contemplated wherein no crease 500 is made.) The crease 500 is preferably formed in the central region 315 between the activated zones 310 and 312. The crease 500 may be formed by any method known in the art, including folding, perforating, scoring, etching or the like. Further, the crease 500 may be made at any desired point in the method of the present invention. In especially preferred embodiments, the crease 500 is formed after the fastening elements 450 have been joined to the laminate 200. The crease helps ensure that the laminate 200, including the fastening elements 450, will be easily folded along the desired path despite any differences in resistance to folding that may exist in the materials along the crease 500.

After the laminate 200 has been activated, and preferably after the intermediate cuts 400 have been made, the folding mechanism 140 folds the laminate 200 upon itself. The fold 510 preferably extends generally parallel to the machine direction to form two overlapping layers of the laminate 200. In preferred embodiments, the fold 510 extends generally in the central region 315, between the first and second activated zones 310 and 312. If the laminate 200 has been creased, as described above, the fold 510 preferably follows the crease 500. As noted above, when the laminate 200 is folded, at least a portion of the laminate 200 overlaps itself. Preferably, at least a portion of the first activated zone 310 overlaps at least a portion of the second activated zone 312. In an especially preferred embodiment, the laminate 200 is folded along its longitudinal centerline L such that the laminate's longitudinal edges 250 are adjacent one another. Also, if the laminate has registration holes 410, it may be desirable to align the registration holes 410 when the laminate 200 is folded. One suitable mechanism for folding the laminate 200 is a folding board, such as those well known in the art. However, any method may be used to fold the laminate 200.

Figure 3E:
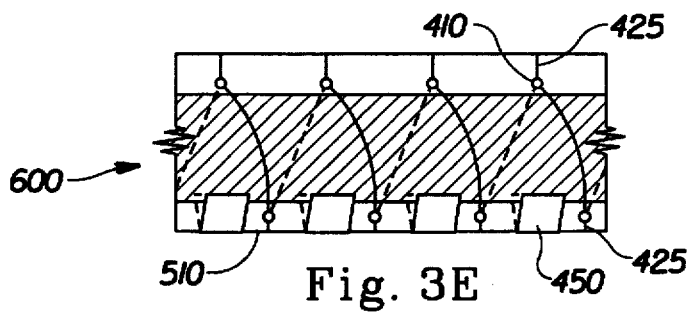

Once the laminate 200 has been folded, it may be desirable to join the side panel stock 600 adjacent the fold 510. This may help add strength to the region to which the fastening element 450 will be joined or may provide a better surface for joining the fastening element 450. Preferred embodiments of side panel stock 600 are shown in FIGS. 3E, 4E and 6E. (Although the side panel stock 600 is shown to comprise the fastening elements 450, as described above, embodiments are contemplated wherein the fastening elements 450 are joined to the laminate 200 once it has been formed into side panel stock 600.) The side panel stock 600 may be fed into a storage container, onto a storage roll 150, as shown in FIGS. 2 and 5, or may be further processed into the individual side panels 30.

Figure 3F:
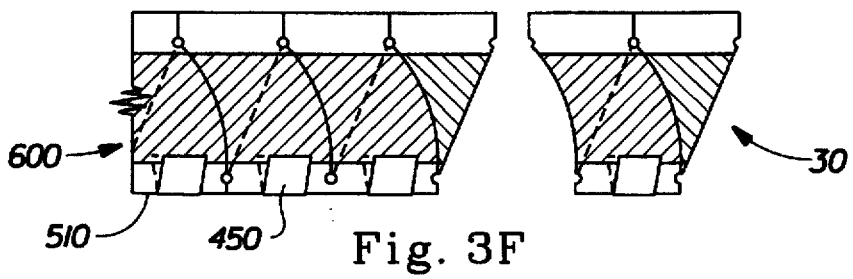

Individual side panels 30 are formed from the side panel stock 600 by separating the side panel stock at predetermined locations. In one preferred embodiment, the laminate 200 is perforated, scored or slit along regions identified as the final cuts 425. The final cuts 425 may be made to separate the individual side panels 30 or may be made prior to the side panel separation. In embodiments wherein the final cuts 425 are made prior to separation of the side panel stock into individual side panels 30, separation of the side panel stock 600 may include applying a force to the regions of the final cuts 425 to separate the side panels 30 from the side panel stock 600. In other embodiments, wherein the side panel stock has not been previously cut or scored, it is necessary to cut, slit or otherwise separate the side panel stock 600. Preferably final cutting device 160 makes final cuts 425, as shown in FIGS. 3E–F, 4E–F, and 6E–F. The final cutting device 160 may be any device known in the art that may cut, slit, perforate or otherwise separate side panel stock 600. In preferred embodiments wherein the side panel stock comprises registration holes 410, the final cuts 425 extend from the registration holes 410 adjacent the longitudinal edges 250 to the longitudinal edges 250 of the laminate. If registrations holes 410 were cut or punched into the laminate 200 in or adjacent to the central zone 315, preferred final cuts 425 extend from those registration holes 410 through the fold 510. Examples of preferred individual side panels 30 are shown in FIGS. 3F, 4F and 6F.

After the individual side panel 30 are separated from the side panel stock 600, they may be joined to an absorbent article such as the one shown in FIG. 1. In a preferred embodiment, the proximal edge 40 of a side panel 30 is joined along each side edge 35 of the diaper 20 in at least a portion of the rear waist region 54. The proximal edge 40 may be joined to the topsheet 22, the backsheet 24 or both and may be located on the outer surface of the backsheet 24, the inner surface of the topsheet 22 or between the topsheet 22 and the backsheet 24. The side panel 30 may be joined to the diaper 20 by any means known in the art, including but not limited to, adhesives, heat bonding, pressure bonding, ultrasonic bonding or any combination thereof.

FIGS. 6A–F show one embodiment of the present invention wherein the side panel stock 600 is preferably cut continuously in a direction generally parallel to the machine direction. (As used herein, the terms "continuous" or "continuously" may include slits, perforations, or the like.) The longitudinal cut 430 preferably is located in the central region 315 adjacent he activated zones 310 and 312. In a preferred embodiment, the intermediate cuts 400 extend from each longitudinal edge 250 across one of the activated zones 310 and 312 into the central region 315. Once the laminate 200 is folded, as shown in FIG. 6E, the longitudinal cut 430 can be made. The longitudinal cut 430 preferably intersects with each of the intermediate cuts 400 in the central region 315. This longitudinal cut 430 acts as a final cut in this embodiment and severs the web such that it may be separated into individual side panels 30. Of course, the longitudinal cut 430 could be straight, curved, irregular, or intermittent, as in the case of perforations. If the longitudinal cut 430 is a series of perforations, the side panel stock 600 may be gathered and stored without separating the side panel stock 600 into side panels 30 until the scrap 440 is removed at a later time.

Figure 7:
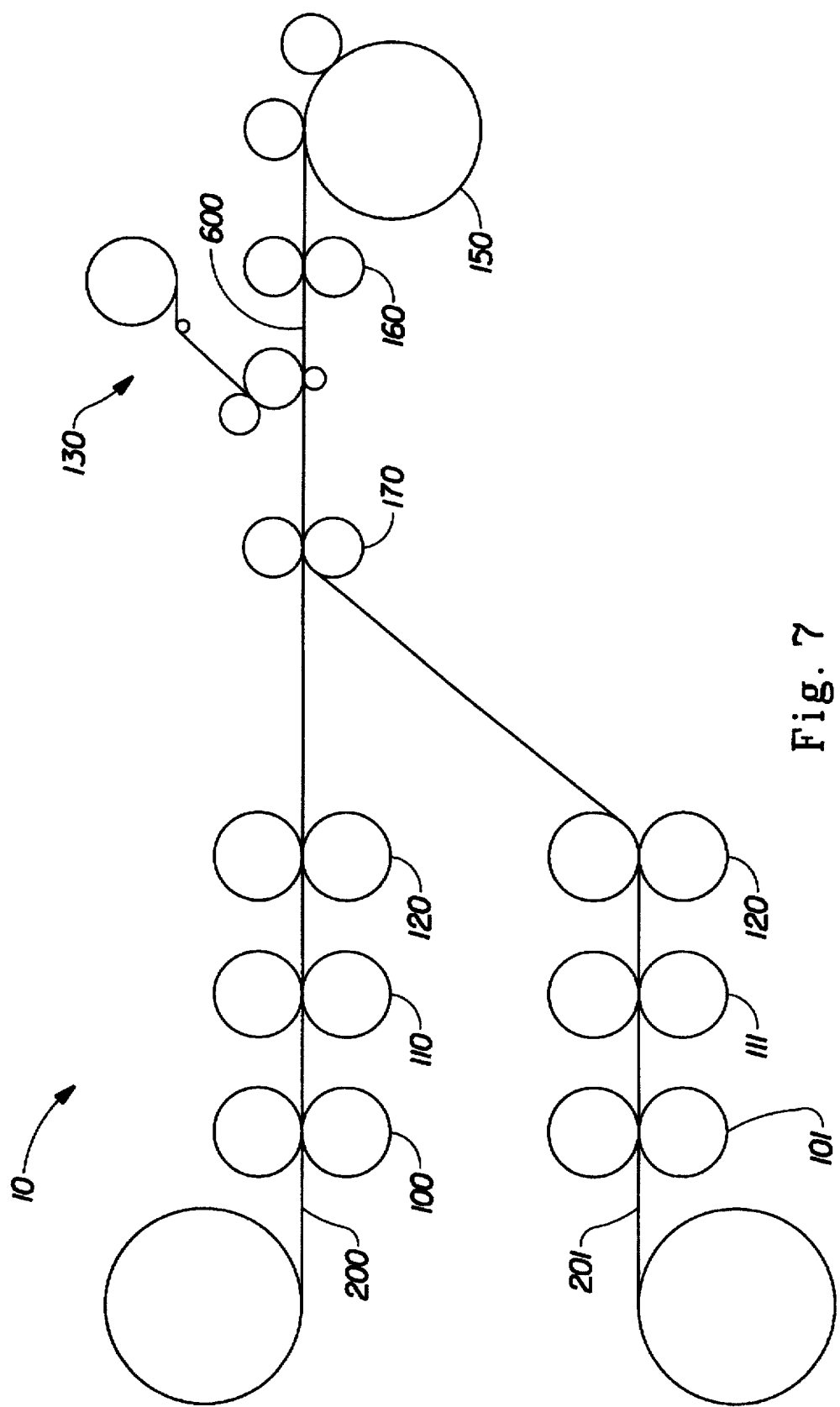
FIG. 7 is a schematic view of one alternative embodiment of the side panel making process.
Figure 8:
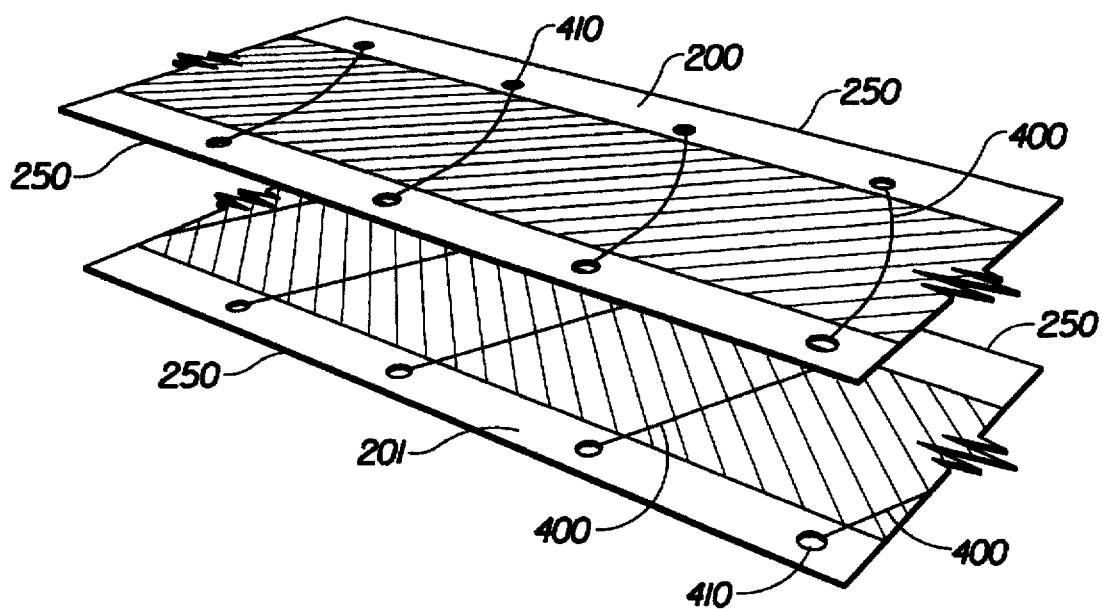
FIG. 8 is a perspective view of a portion of one embodiment of the method shown in FIG. 7.

FIG. 7 depicts an alternative embodiment of the process of the present invention. In the alternative embodiment shown, two separate webs 200 and 201 are joined to form the side panel stock 600. As described above, the webs 200 and 201 may be manufactured on line or may be made at a different time or place from the subsequent process of making individual side panels 30. In one preferred embodiment, as shown in FIG. 7, two webs 200 and 201 are unwound from storage rolls prior to entering the side panel manufacturing apparatus 10. The webs 200 and 201 may comprise any suitable single material or laminate of materials that will provide the desired characteristics in the finished side panels 30. Suitable laminates are described above with regard to other embodiments of the present invention. The webs or laminates 200 and 201 may be the same or different, and thus, may provide a wide range of characteristics in each individual side panel 30. Further, by changing one or more of the webs 200 or 201, the method can provide very different side panels 30 made by the same process and apparatus.

As shown in FIG. 7, each web 200 and 201 is generally fed into the process by any means known in the art, including the hose previously described. Preferably, the webs 200 and 201 pass through tensioning and metering devices before proceeding to the tracking devices 100 and 101. The tracking devices 100 and 101 may be any known tracking devices and are described in greater detail above. Registration holes may be punched or cut into either or both of the webs 200 or 201 to help align the webs for further processing. One or both of the webs 200 and/or 201 may be activated as described above by an activating device 110 or 111. The activating devices 110 or 111, if any, may be any suitable device known in the art. Examples of preferred activation processes are described above. The webs 200 and 201 are preferably subjected to a series of intermediate cuts 400 prior to being combined with one another. The intermediate cuts 400 may be any suitable cuts, slits, perforations, etc., as described above with regard to any of the other embodiments of the present invention. (It should be noted that the order of the preceding steps may be varied to best meet the needs of the user. Also, any of the steps may be performed off-line prior to the time at which either or both of the webs 200 and 201 are fed into the side panel making apparatus 10.)

After the webs 200 and 201 have been activated (if at all) and have received their respective intermediate cuts 400, the webs 200 and 201 are preferably joined together. As shown in FIG. 7, the webs preferably pass through a joining mechanism 170 which brings the webs 200 and 201 in contact with each other in at least a partially overlapping configuration. In one preferred embodiment, the webs 200 and 201 are generally fully overlapping such that their corresponding longitudinal edges 250 are generally adjacent each other. Preferably, at least one overlapping pair of longitudinal edges 250 is joined to form the side panel stock 600. Any suitable joining means may be used to join the webs, including, but not limited to adhesives, cohesives, mechanical bonds, ultrasonic bonds, pressure bonds, heat bonds and any combination of the preceding means. Further, additional materials may be added to the bond region to add strength or to provide other benefits to the side panel stock 600. One means of joining the webs 200 and 201 is to join the fastening elements 450 so as to hold the webs 200 and 201 together. However, the fastening elements 450 may be joined to the side panel stock 600 after the longitudinal edges 250 have been joined or may be left off entirely.

Individual side panels 30 are formed from the side panel stock 600 by separating the stock 600 at the predetermined final cut regions. The final cutting mechanism 160 may be any cutting means known in the art, including those described above with regard to the making of the final cuts 425. Otherwise, the side panel stock 600 may be fed into a storage container or wound onto a roll, such as roll 150 such that it may be further processed at a later time or in a different location.

While particular embodiments of the present invention have been illustrated and described, it would be obvious to those skilled in the art that various other changes and modifications could be made without departing from the spirit and scope of the invention. It is therefore intended to cover in the appended claims all such changes and modifications that are within the scope of this invention.

What is claimed is:

1. A method for manufacturing extensible side panels for disposable articles, the method comprising the steps of:
   (a) providing a web of material in a machine direction, said web having a longitudinal centerline generally parallel to said machine direction, a pair of longitudinal edges, designated final cut regions, a first region, a second region, and a central zone, said central zone disposed between said first region and said second region;
   (b) making a series of intermediate cuts in said web, each of said intermediate cuts extending across at least a portion of one of said first or second regions;
   (c) folding said web along an axis that is generally parallel to said machine direction 10 form a folded web; and
   (d) cutting said folded web in said designated final cut regions to produce individual extensible side panels.

2. The method according to claim 1 further comprising the step of activating a first activation zone disposed in at least said first region.

3. The method according to claim 2 further comprising activating a second activation zone disposed in said second region.

4. The method according to claim 3 wherein said activation zones extend generally in said machine direction.

5. The method according to claim 3 wherein said first and said second activation zones are laterally spaced apart about said central zone, at least a part of said central zone being coincident with said axis along which said web is folded.

6. The method of claim 5 further comprising the step of providing registration holes in said web.

7. The method according to claim 3 wherein said step (b) of making a series of intermediate cuts comprises making a series of first intermediate cuts and a series of second intermediate cuts, said first intermediate cuts extending across at least a portion of said first activation zone but not extending into said second activation zone and said second intermediate cuts extending across at least a portion of said said second activation zone but not extending into said first activation zone.

8. The method according to claim 1 wherein said step (b) of making a series of intermediate cuts comprises making a series of first intermediate cuts and a series of second intermediate cuts, said first intermediate cuts extending across at least a portion of said first region but not extending into said second region and said second intermediate cuts extending across at least a portion of said second region but not extending into said first region.

9. The method according to claim 8 wherein said first intermediate cuts are uniformly spaced apart in said machine direction.

10. The method according to claim 9 wherein said second intermediate cuts are uniformly spaced apart in said machine direction.

11. The method according to claim 10 wherein said first and said second intermediate cuts are offset from each other in said machine direction.

12. The method of claim 1 further comprising the step of providing registration holes in said web.

13. The method according to claim 1 wherein said intermediate cuts are at an angle to said machine direction.

14. The method according to claim 1 wherein said intermediate cuts are generally curvilinear.

15. The method according to claim 1 further comprising the steps of joining a fastening member to said web.

16. The method according to claim 15 wherein at least a portion of said fastening member is joined to said web in at least a portion of said central zone.

17. The method according to claim 16 wherein said fastening member is joined to said web before said step (c) of folding said web.

18. The method according to claim 16 wherein said fastening member is joined said web after said step (c) of folding said web.

19. The method according to claim 1 wherein said step (b) of making a series of intermediate cuts comprises slitting or perforating said web such that said web is not completely severed by said intermediate cuts.

20. The method according to claim 19 wherein said intermediate cuts extend from one of said longitudinal edges of said web to the other of said longitudinal edges.

21. The method according to claim 1 wherein said step (d) of cutting said folded web in said designated final cut regions comprises slitting or perforating said folded web in said final cut regions such that said web is not completely severed in said final cut regions.

22. The method according to claim 1 wherein said step (d) of cutting said folded web in said designated final cut regions comprises making a continuous cut generally parallel to said longitudinal edges of said folded web, said continuous cut intersecting with the intermediate cuts.

23. A method for manufacturing extensible side panels for disposable articles, the method comprising the steps of:
   (a) providing a web of material in a machine direction, said web having a longitudinal centerline generally parallel to said machine direction, a pair of longitudinal edges, designated final cut regions, a first region, a second region and a central zone, said central zone disposed between said first region and said second region;
   (b) providing registration holes in said web;
   (c) making a series of first intermediate cuts and a series of second intermediate cuts, said first intermediate cuts extending across said first region from one of said registration holes disposed adjacent said longitudinal edge adjacent said first region to one of said holes registration disposed in said central zone adjacent said first region and said second intermediate cuts extending across said second region from one of said registration holes disposed adjacent said longitudinal edge adjacent said second region to one of said registration holes disposed in said central zone adjacent said second region;

(d) folding said web along an axis that is generally parallel to said machine direction to form a folded web; and (e) cutting said folded web in said designated final cut regions to produce individual extensible side panels.

24. A method for manufacturing extensible side panels for disposable articles, the method comprising the steps of:

(a) providing a web of material in a machine direction, said web having a longitudinal centerline generally parallel to said machine direction, a pair of longitudinal edges, designated final cut regions, a first region, a second region and a central zone, said central zone disposed between said first region and said second region, at least a portion of said central zone being coincident with an axis;

(b) activating a first activation zone disposed in at least said first region;

(c) activating a second activation zone disposed in said second region, said first and said second activation zones being laterally spaced apart about said central zone;

(d) providing registration holes in said web;

(e) making a series of first intermediate cuts and a series of second intermediate cuts, said first intermediate cuts extending across said first activation zone from one of said registration holes disposed adjacent said longitudinal edge adjacent said first activation zone to one of said registration hole disposed in said central zone adjacent said first activation zone and said second intermediate cuts extending across said second activation zone from one of said registration holes disposed adjacent said longitudinal edge adjacent said second activation zone to one of said registration holes disposed in said central zone adjacent said second activation zone;

(f) folding said web along said axis that is generally parallel to said machine direction to form a folded web; and (g) cutting said folded web in said designated final cut regions to produce individual extensible side panels.

25. A method for manufacturing extensible side panels for disposable articles, the method comprising the steps of:

(a) providing a first web of material in a machine direction, said first web having a pair of longitudinal edges generally parallel to said machine of said first web direction and designated final cut regions;

(b) providing a second web of material in a machine direction, said second web having a pair of longitudinal edges generally parallel to said machine direction of said second web and designated final cut regions;

(c) making a series of intermediate cuts in said webs;

(d) overlapping said first web and said second web such that at least one of said longitudinal edges of said first web generally overlaps at least one of said longitudinal edges of said second web;

(e) joining at least a portion of each of said first and said second webs adjacent said overlapping longitudinal edges to form a side panel stock; and (f) cutting said side panel stock in said designated final cut regions to produce individual extensible side panels.

26. The method according to claim 25 further comprising the step of activating a predetermined activation zone located in at least said first web.

27. The method according to claim 26 further comprising the step of activating a predetermined activation zone located in said second web.

28. The method according to claim 27 wherein said first and said second activation zones extend generally in said machine direction.

29. The method of claim 25 further comprising the step of providing registration holes in at least said first web.

30. The method of claim 29 wherein said registration holes are disposed adjacent said longitudinal edges of said first web.

31. The method of claim 30 wherein said intermediate cuts extend across said first web between said registration holes disposed adjacent said longitudinal edges.

32. The method according to claim 25 wherein said intermediate cuts are at an angle to said machine direction.

33. The method according to claim 25 wherein said intermediate cuts are generally curvilinear.

34. The method according to claim 25 further comprising the steps of joining a fastening member to said side panel stock.

35. The method according to claim 25 wherein said step (c) of making a series of intermediate cuts comprises slitting or perforating said webs such that said webs are not completely severed by said intermediate cuts.

36. The method according to claim 35 wherein said intermediate cuts extend from one of said longitudinal edges of each of said webs to the other of said longitudinal edges.

37. The method according to claim 25 wherein said step (f) of cutting said side panel stock in said designated final cut regions comprises slitting or perforating said side panel stock in said final cut regions such that said panel stock are not completely severed in said final cut regions.

38. The method according to claim 25 said step (f) of cutting said said side panel stock in said designated final cut regions comprises making a continuous cut generally parallel to said longitudinal edges of said folded web, said continuous cut intersecting with the intermediate cuts.

* * * * *

UNITED STATES PATENT AND TRADEMARK OFFICE
CERTIFICATE OF CORRECTION

PATENT NO. : 5,683,533
DATED : Nov. 4, 1997
INVENTOR(S) : KEIGHLEY, ET AL.

It is certified that error appears in the above-identified patent and that said Letters Patent is hereby corrected as shown below:

Column 4, line 58, "yams" should read --yarns--.

Column 6, line 18, "mounts" should read --amounts--.

Column 6, line 49, "recostnized" should read --recognized--.

Column 8, line 8, "at." should read --al.--.

Column 11, Claim 1(c), line 40, "10" should read --to--.

Column 13, Claim 24(e), line 32, "hole" should read --holes--.

Column 14, Claim 38, line 52, "folded web" should read --side panel stock--.

Signed and Sealed this

Sixth Day of February, 2001

*Attest:*

Q. TODD DICKINSON

*Attesting Officer*     *Director of Patents and Trademarks*